United States Patent [19]

Kimbrow

[11] Patent Number: 4,737,910
[45] Date of Patent: Apr. 12, 1988

[54] APPARATUS FOR TRACKING INVENTORY

[76] Inventor: Ronald H. Kimbrow, 11030 San Juan, Apt. #C, Loma Linda, Calif. 92354

[21] Appl. No.: 787,533

[22] Filed: Oct. 15, 1985

[51] Int. Cl.⁴ .................................... G06F 15/226
[52] U.S. Cl. ............................ 364/403; 377/13; 235/385
[58] Field of Search ........... 235/383, 385, 491, 381; 364/404, 403; 340/715, 752, 753, 502; 194/216, 217; 221/6, 7; 377/13

[56] References Cited

U.S. PATENT DOCUMENTS

| | | | |
|---|---|---|---|
| 1,071,664 | 8/1913 | Girson . | |
| 1,539,919 | 6/1925 | Swift . | |
| 1,872,782 | 8/1932 | Messick et al. . | |
| 2,663,495 | 12/1953 | Ramsell et al. | 235/61 |
| 3,221,860 | 12/1965 | Klaffky | 194/218 X |
| 3,441,719 | 4/1969 | Haller et al. | 235/92 |
| 3,688,087 | 8/1972 | Howard et al. | 364/403 X |
| 3,694,630 | 9/1972 | Dybel | 235/92 |
| 3,784,802 | 1/1974 | Imai et al. | 364/403 |
| 3,836,755 | 9/1974 | Ehrat | 235/383 |
| 3,959,630 | 5/1976 | Hogberg | 235/491 |
| 3,978,321 | 8/1976 | Doggett | 235/92 |
| 3,984,825 | 10/1976 | Fujita | 340/502 |
| 4,021,644 | 5/1977 | Dreslinski | 235/92 |
| 4,234,869 | 11/1980 | Sandelman | 340/286 |
| 4,392,564 | 7/1983 | Hayashi | 194/218 |
| 4,500,880 | 2/1985 | Gomersall et al. | 340/825.35 |

OTHER PUBLICATIONS

*Basic;* IBM Personal Computer Hardware Reference Library, 2nd Ed.; May 1982; pp. B-12 to B-14.

*Primary Examiner*—David L. Trafton
*Attorney, Agent, or Firm*—Richards, Harris, Medlock & Andrews

[57] ABSTRACT

An apparatus is provided for monitoring inventory in a business or hospital to provide an immediate indication of the number of items in such inventory, the number of items needed to be reordered at any time to replenish the inventory to its maximum level, and the critical minimum inventory level necessitating a stock reorder to avoid depletion of stock before new stock items can arrive from the business' supplier.

1 Claim, 2 Drawing Sheets

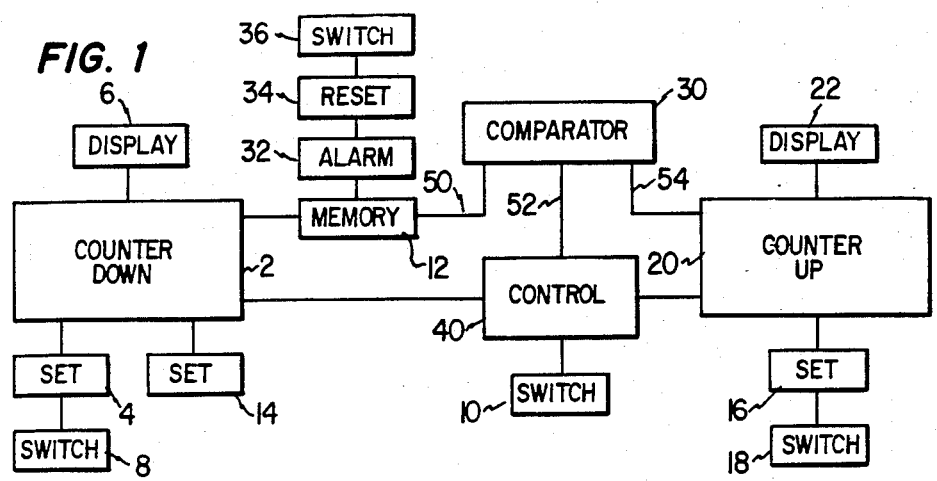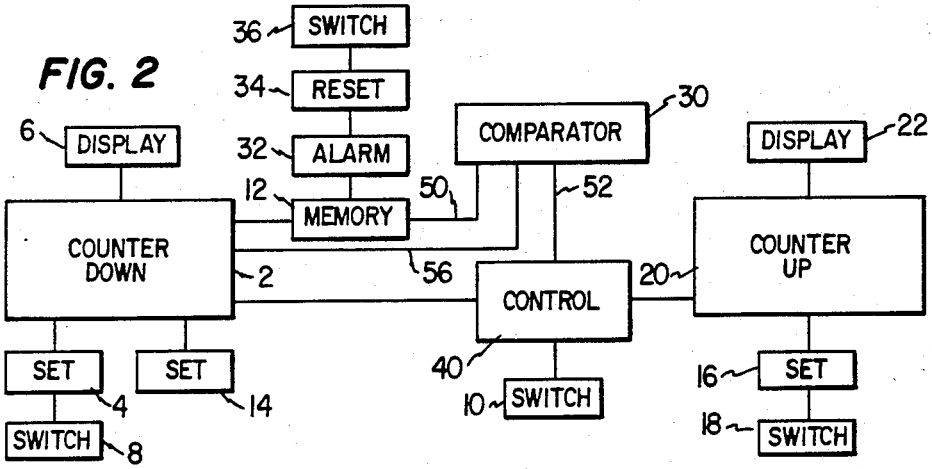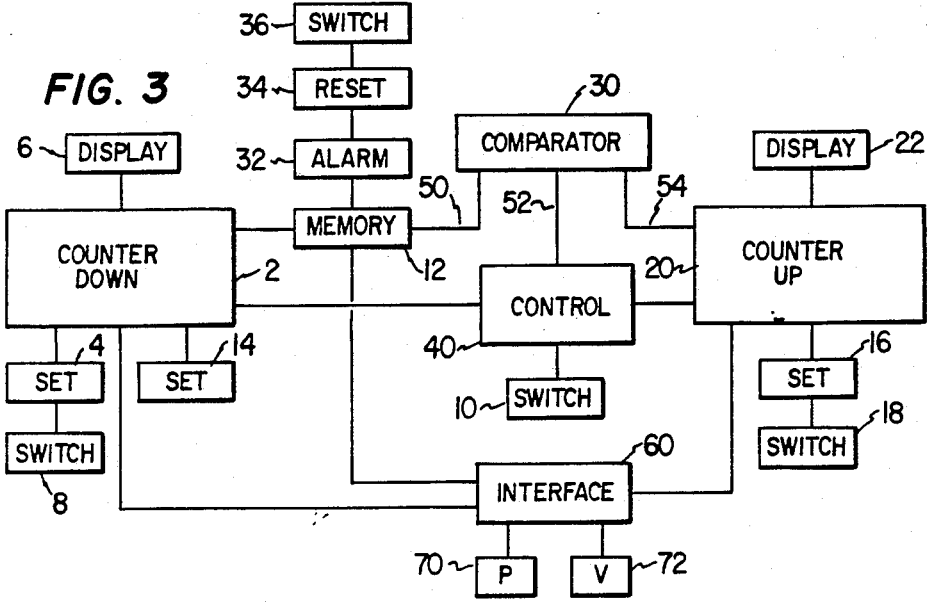

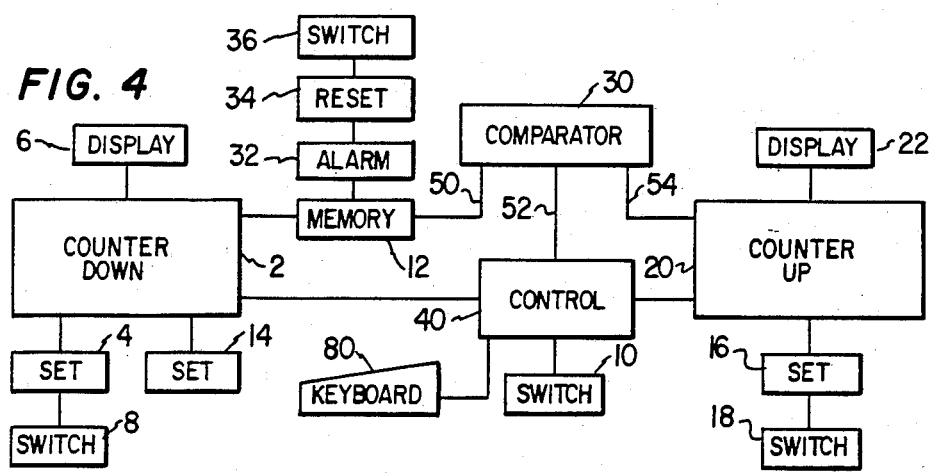
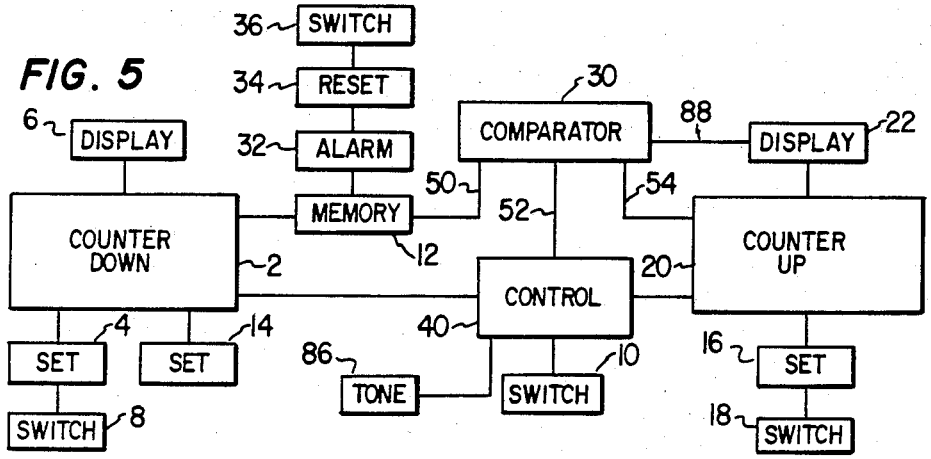
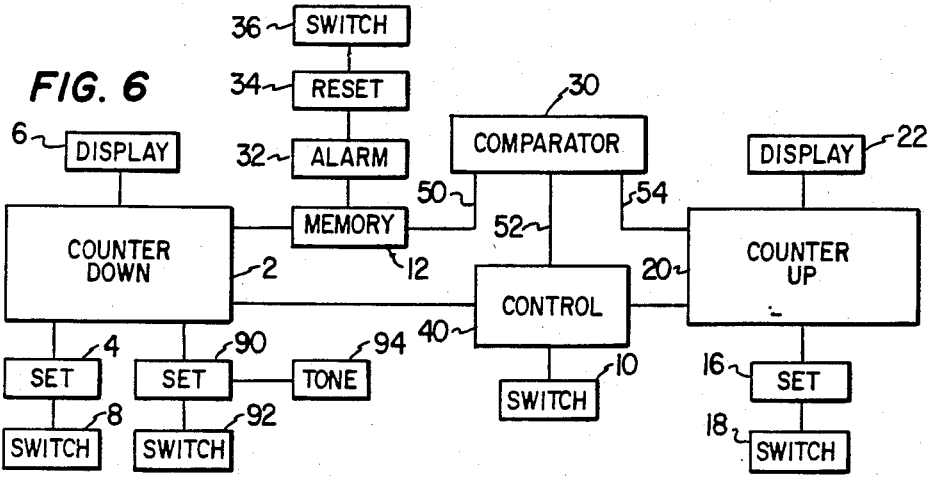

APPARATUS FOR TRACKING INVENTORY

TECHNICAL FIELD

The present invention relates to an apparatus for monitoring inventory to provide an immediate indication at the shelf of the number of items in inventory, the number of items to be reordered to replenish the inventory to its maximum level, and the critical minimum inventory level mandating a stock reorder.

BACKGROUND ART

Normally, business enterprises stock items of inventory so that the items are immediately available to customers upon demand without the need for ordering them from the business' source when the customer makes his purchase. It is a common occurrence for the number of items in inventory to be reduced by sales to the point at which it would be impossible for the business enterprise to timely reorder inventory to avoid completely running out of stock prior to new stock arriving from its supplier. In particular, stock may be reduced below a critical amount and then reordered only to become completely depleted before the ordered shipment can arrive from the supplier. Likewise, the same problem is present in hospitals and in military operations where the depletion of inventory supplies can have catastrophic results.

The prior art includes various mechanical stock registers that record and display the number of items taken from stock, and display the number of items presently in stock. U.S. Pat. No. 1,539,919 to Swift discloses a stock register for registering quantities of commodities presently in stock, and for counting quantities as taken from stock. U.S. Pat. No. 2,663,495 to Ramsell et al., discloses an electrical apparatus for selectively computing and keeping count of inventory of a number of different items of manufacture as they are produced and disposed of, and also for giving a current record of unfilled orders.

In addition, the prior art discloses many devices for monitoring the number of items or people within a closed or confined area. Specifically U.S. Pat. No. 1,872,782 to Messick, et al. discloses a registering device to tally the number of people in a railroad car; and U.S. Pat. No. 3,978,321 to Doggett discloses a portable hand-carried automobile counting device for monitoring the number of cars in a parking lot.

Finally, U.S. Pat. No. 4,500,880 to Gomersall, et al. discloses a computer driven informational display system adapted for use with the standard Universal Product Code to display pricing and other associated information regarding shelf inventory.

SUMMARY OF THE INVENTION

This invention contemplates an apparatus that can be mounted proximate to a shelf containing a specified inventory of items and has at least a single visual display indicating the number of items needed to be reorderd to rejuvenate said inventory to its maximum level and a means for announcing a critical minimum inventory at the point where inventory must be reordered in order to avoid a complete depletion of inventory before delivery of new items. In the preferred embodiment, this invention comprises an apparatus having two displays, the first as being described above, and a second indicating the number of items presently on hand. This preferred device is user operated by the person removing stock by touching a button on said apparatus as stock is removed to increment the display showing the number of items to be reordered and decrement the display showing the number of items on hand. The critical minimum number of inventory items is preset by the user and is determined by the user's experience for a particular stock item.

BRIEF DESCRIPTION OF THE DRAWINGS

For a more complete understanding of the present invention and for further advantages thereof, reference is now made to the following Detailed Description taken in conjunction with the accompanying Drawings, in which FIGS. 1-6 are block diagrams of alternative embodiments of the present invention.

DETAILED DESCRIPTION

The present invention contemplates an apparatus for monitoring inventory to provide an immediate indication of the number of items in said inventory, the number at the shelf of items to be reordered to replenish the inventory to its maximum level, and the critical minimum inventory level mandating stock reorder to avoid a complete depletion of inventory before the reordered items can arrive from the supplier.

In the preferred embodiment, the present invention is an electronic device having two liquid crystal displays. A first display shows the exact number of items presently in inventory, and a second display shows the number of items needed to be reordered to replenish said inventory to its maximum level. This embodiment is user operated by the person removing stock pushing a button or switching a switch on said device once for each item removed which decrements said first display reflecting the number of items on hand, and increments the display showing the number of items to be reordered. When said button is pushed or switched a beep tone is emitted from an annunciator to announce the removal of inventory Additionally, the present invention provides for the preprogramming of said apparatus to announce the point at which a critical minimum inventory level is reached by the user entering this critical number into a memory unit, denoting the point where inventory must be reordered to avoid a complete depletion of stock before new stock can arrive from the supplier. The present invention also has a means for setting the first display reflecting the number of items on hand, and setting the display showing the number of items to be reordered to zero when stock is replenished to its maximum level.

In an alternative embodiment, the above described apparatus is linked to a computer printout device or video display allowing the remote audit of a particular inventory. It will be understood that each particular stock item in inventory would have a separate device associated with it, and that all such devices for a particular business or enterprise could be monitored simultaneously on said printout or video means. Further, the liquid crystal display described above could also be a light emitting diode or a mechanical numeric display.

Additionally, it will be understood that instead of a user operated switch simultaneously decrementing and incrementing the above said registers, a mechanical switch triggered by the removal of an item from inventory can be used, as well as, but not limited to, an optical detector; a piezoelectric detector; a weight sensor detector; a radiation detector; and a Universal Product Code reader. Further, a calculator keyboard device can be used to allow the user to register the removal of items in multiple numbers.

In the preferred embodiment, when the preset critical minimum inventory level is reached the apparatus of the present invention will emit an intermittent audio tone or beeping sound and the display showing the number of items to be reordered will flash on and off in coordination with said beeping tone. It will be understood that alternative embodiments contemplate, but are not limited to, a single audio tone, and a flashing light source. Additionally, it will be understood that the announcement of an inventory's being at its critical minimum level can also be made on a remote announcing device, such as the computer printout and video means described above.

As shown in FIG. 1, counter 2 is initially set by set means 4 and is linked to display 6. Counter 2 is a down counter and serves to keep track of the number of items in inventory as they are removed. During operation, display 6 displays the number of items in inventory. Counter 2 is set by pushing said set means 4 which comprises a button and holding switch means 8 down while counter 2 advances to the number corresponding to the number of items in inventory, at which time the user releases switch 8 and counter 2 becomes fixed until decremented by operation of switch 10.

Prior to operation, memory 12, intended to store the critical minimum number of items in inventory as described above, is set by triggering switch 14 which changes the mode of counter 2 and display 6 to display the contents of memory 12. Counter 2 is then allowed to advance to the critical minimum number of inventory items at which time switch 14 is released and this number is stored in memory 12. Alternatively, if the number stored in memory 12 is to be decreased, switch 14 can be depressed while simultaneously depressing switch 10 to decrement the contents of counter 2. Similarly, when switch 14 is released the contents of counter 2 is loaded into memory 12. Setting means 16 is controlled by switch 18 and serves to zero counter 20, said counter being an up counter. Counter 20 is linked to display 22 which shows the number of items needed to be reordered at any point in time to replenish the inventory to its maximum level. Counter 20 can be zeroed either before or after the contents of counter 2 and memory 12 are set.

During operation, the contents of counter 20 and memory 12 are compared by comparator 30. When the contents of counter 20 and memory 12 are found to be equal, alarm 32 is triggered and sounds a beep or other intermittent audio tone until reset by reset means 34 operated by switch 36. Operation of reset means 34 does not serve to alter the contents of either counters 2 or 20, nor alter the contents of memory 12. Switch 10 can continue to be operated after alarm 32 has been silenced. Conductor 50 serves to connect memory 12 and comparator 30; conductor 52 connects control 40 and comparator 30; and conductor 54 connects up counter 20 and comparator 30.

In operation, switch 10 is depressed by the user and signals control 40 to both decrement counter 2 reflecting that an item has been removed from inventory and increment counter 20 reflecting that at least one more item of inventory needs to be reordered to replenish the inventory to its maximum amount. Control 40 also serves to trigger comparator 30, which then proceeds to compare the contents of memory 12 and counter 20.

As shown in FIG. 2, an alternative embodiment of the present invention has comparator 30 compare the contents of memory 12 with the contents of down counter 2. Conductor 50 connects memory 12 with comparator 30; conductor 52 connects control 40 with comparator 30; and conductor 56 connects down counter 2 with comparator 30. In operation of this embodiment, the contents of downcounter 2 and memory 12 are compared by comparator 30. When the contents of counter 2 in memory 12 are found to be equal, alarm 32 is triggered and sounds a beep or other intermittent audio tone until reset by reset means 34 operated by switch 36. Operation of reset means 34 does not serve to alter the contents of either counters 2 or 20, nor alter the contents of memory 12. Switch 10 can continue to be operated after alarm 32 has been silenced.

In yet another embodiment, as shown in FIG. 3, interface means 60 is connected to down counter 2 via conductor 62 to memory 12 by conductor 64 and to up counter 20 by conductor 66. Interface means 60 serves to interface the apparatus of the present invention with printer 70 and video display 72. Printer 70 and video unit 72 serve as means to remotely monitor the status of a particular inventory's current state, the number of items to be reordered, and the critical reorder number.

As inventory items are removed from stock the user pushes switch 10 once for each item removed which causes the device to reflect the exact number of units remaining on hand and the exact number of units needed to be reordered at that particular time to replenish inventory to its maximum level. For instance, if a stock boy removes five items from inventory he pushes the button five times to decrement the first display five units and increment the second display five units. After a time, the inventory will reach its critical minimum level and the device will sound a constant beeping sound until a reset button is pushed. Eliminating the audio alarm does not change the numbers shown on both displays, and inventory can continue to be removed from stock. At the point at which the alarm sounds, the user is alerted to the fact that he must immediately reorder the number of items shown on the reorder display so that his stock will not be depleted before his reordered items can arrive from his supplier.

As shown in FIG. 4, an alternative embodiment contemplates keyboard 80 linked to control 40, whereby the user is able to enter the number of items removed from inventory on said keyboard and then press switch 10 whereby counter 2 is decremented the same number in a single step and counter 20 is incremented the same number in a single step. For instance, if the user seeks to remove 100 items from inventory he may enter the number "100" on keyboard 80 and press switch 10. Counter 2 is instantly decremented 100 units and counter 20 instantly incremented 100 units. Keyboard 80 is intended to alleviate the need for pressing switch 10 many times if many items are removed from inventory, transforming these steps into a single operation on switch 10.

As shown in FIG. 5, control 40 is linked to tone means 84 which serves to announce each time switch 10 is pressed. Such announcement can comprise a beeping sound or other audible sound to indicate that an item has been removed from inventory. When kekyboard 80 (as shown in FIG. 4) is employed, tone 86 will occur only once each time switch 10 is presed, regardless of the number entered on said keyboard. Further, comparator 30 is linked to display 22 by conductor 88, causing display 22 to flash on and off when the contents of memory 12 is equal to the contents of up counter 20 (as shown in FIG. 5) or in an alternative embodiment when the contents of memory 12 is equal to the contents of down counter 2 (as shown in FIG. 2).

As shown in FIG. 6, set means 14 (as shown in FIGS. 1 through 5) is eliminated and replaced by set means 90 which is activated by switch 92. Set means 90 serves to load the contents of counter 2 into memory 12. In operation, set means 4 operates to advance the value of counter 2. When the value of counter 2, shown on display 6, reaches the amount which has been determined to be the critical reorder number, switch 92 is activated which causes set means 90 to load the contents of counter 2 into memory 12. Switch 8 is then reactivated which causes counter 2 to further advance to the maximum inventory level. Activation of set means 90 triggers audio tone 94 to confirm to the user that the contents of counter 2 have been loaded into memory 12.

In an alternative embodiment, several hundred of such inventory tracking devices can be used with a remote video display and computer printout device in a warehouse allowing a manager to constantly monitor the number of items in stock, and coordinate his reorder schedules for the various items. Each morning a computer printout device can deliver to the manager a document reflecting which items need to be reordered, and how many of each item need to be reordered to avoid the depletion of the warehouse's supplies. Further, a computer printer can be used in conjunction with the present invention to generate the actual reorder requests and directly mail such to the supplier without human intervention.

While certain embodiments of the present invention have been described in detail herein, it will be evident that various further modifications are possible without departing from the scope of the invention.

What is claimed is:

1. An apparatus for continuously monitoring the number of discrete items in an inventory, comprising:
   a first counter located at the site of the inventory, said first counter storing a first count of the number of items on hand in the inventory and having a first display for continuously indicating the number of items on hand;
   a second counter located at the site of the inventory, said second counter storing a second count of a reorder quantity necessary to fill the inventory and having a second display for continuously indicating said reorder quantity;
   a control connected to said first and second counters, said control having a means for decrementing said first count and incrementing said second count when items are removed from the inventory and for incrementing said first counts and decrementing said second count when items are restocked in the inventory;
   a memory connected to said first counter for storing a critical minimum number indicating a mandatory reorder condition for items in the inventory;
   a comparator connected to said memory for comparing said first count of items on hand with said critical minimum number; and
   an alarm connected to said memory for providing a signal when said first count of items on hand is decremented to said critical minimum number.

* * * * *